United States Patent [19]

Moore, Jr.

[11] 3,933,775

[45] Jan. 20, 1976

[54] 2[(1-CYANO-1-METHYLETHYL)AZO]-2-METHYLPROPIONAMIDE

[75] Inventor: Earl P. Moore, Jr., Wilmington, Del.

[73] Assignee: E. I. Du Pont de Nemours and Company, Wilmington, Del.

[22] Filed: Mar. 5, 1974

[21] Appl. No.: 448,364

Related U.S. Application Data

[62] Division of Ser. No. 357,524, May 7, 1973.

[52] U.S. Cl.... 260/89.1; 260/88.7 R; 260/89.5 AW; 260/88.7 D; 260/85.5 F; 260/93.5 W; 260/92.8 W; 260/94.6

[51] Int. Cl.² ............ C08F 118/08; C08F 120/44; C08F 114/06; C08F 120/12

[58] Field of Search......... 260/88.7 R, 89.1, 88.7 D, 260/85.5 F, 89.5 AW, 93.5 W, 94.6, 92.8 W

[56] References Cited

UNITED STATES PATENTS

| | | | |
|---|---|---|---|
| 2,520,338 | 8/1950 | Robertson | 260/93.5 W |
| 2,877,102 | 3/1959 | Levesque | 260/192 |
| 2,923,694 | 2/1960 | Schmidt | 260/88.7 D |
| 3,309,297 | 3/1967 | Takayama et al. | 260/192 |
| 3,642,751 | 2/1972 | Logemann et al. | 260/88.7 D |

*Primary Examiner*—Joseph L. Schofer
*Assistant Examiner*—Maria S. Tungol

[57] ABSTRACT

2-[(1-Cyano-1-methylethyl)azo]-2-methylpropionamide is provided as a unique compound for catalyzing the polymerization of ethylenically unsaturated compounds.

8 Claims, No Drawings

2[(1-CYANO-1-METHYLETHYL)AZO]-2-METHYLPROPIONAMIDE

BACKGROUND OF THE INVENTION

This application is a divisional of my copending application Ser. No. 357,524, filed May 7, 1973.

Organic and inorganic peroxygen compounds, such as peroxides, hydroperoxides, peresters, persulfates, hydrogen peroxide etc. are widely employed as free-radical initiators in polymerizations of ethylenically unsaturated compounds. However, peroxygen initiators have shortcomings which limit their usefulness; they often oxidize polymers or leave oxygenated residues which cause discoloration on aging and light sensitivity; they alter the color of dyestuffs; many are shock sensitive and unpredictable in behavior; they can cause undesirable chain-branching.

On the other hand, azo initiators such as the azonitriles disclosed in U.S. Pat. No. 2,471,959 and compounds derived from them do not have the undesirable characteristics ascribed to peroxides and are highly useful in vinyl polymerizations. Azo initiators which are both soluble and insoluble in water find utility. However, most water soluble azo compounds are acids and their salts as disclosed, for example, in U.S. Pat. No. 2,520,338 and amidine salts as disclosed, for example, in U.S. Pat. No. 2,599,300 and the like. Such compounds can introduce functional groups into polymers which reduce thermal stability as well as detract from physical, electrical and mechanical properties. However, water insoluble azo compounds frequently do not have desirable free-radical initiation properties in aqueous polymerization systems of the emulsion and dispersion types. Induction times, that is, the time it takes to initiate the polymerization of the ethylenically unsaturated compound using water insoluble azo compounds may be much longer than the induction times involved when water soluble azo initiators are used.

SUMMARY OF THE INVENTION

As a new compound this invention provides 2-[(1-cyano-1-methylethyl)azo]-2-methylpropionamide which has the structure

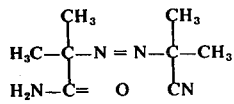

When employed in catalytic quantities, that is, any quantity effective to initiate the polymerization reaction, the unique compound of this invention functions as an excellent catalyst for the polymerization of ethylenically unsaturated compounds. Indeed, as little as 0.01% by weight based on the weight of the monomers easily and effectively initiates the polymerization of any desired ethylenically unsaturated monomers. Generally from about 0.01 to about 2% by weight based upon the weight of the monomers is employed, preferably 0.05 to 0.5% by weight.

The unique compound of this invention is new, effective, water soluble, neutral, inexpensive and easy to prepare from readily available starting materials. Aqueous solution as well as dispersion or emulsion polymerization of ethylenically unsaturated compounds can be carried out with induction or initiation times as short as a few minutes when the azomonoamide of this invention is used as opposed to the 1 to 12 hours or more which are frequently required before initiation begins using insoluble azonitriles.

DETAILED DESCRIPTION OF THE INVENTION

The unique azomonoamide compound of this invention is readily prepared by the hydrogen peroxide-promoted basic hydrolysis of $\alpha,\alpha'$-azobisisobutyronitrile which is readily available under the tradename Vazo 64. The $\alpha,\alpha'$-azodiisobutyronitrile is reacted in solution at a maximum concentration of about 20% by weight of the nitrile preferably from 8 to 12% at temperatures of from about 25° to about 50°C. with hydrogen peroxide in the presence of a base to yield 2-[(1-cyano-1-methylethyl)azo]-2-methylpropionamide. Because the starting compound is insoluble in water, the reaction is generally carried out in an alcohol or acetone solution or in a mixture of from about 2:1 alcohol or acetone to water up to 100% of acetone or alcohol and preferably 100% alcohol is employed. Any suitable water miscible alcohol may be employed in the preparation such as, for example, methanol, ethanol, n-propanol, isopropanol, tert-butyl alcohol and the like but preferably methanol is used.

Any suitable base may be used to prepare the azomonoamide of this invention including for example, any alkali metal hydroxide such as sodium, potassium, lithium and the like hydroxides, ammonium hydroxide and so on. The amount of 100% base which is used on a molar basis ranges from about 0.1 mol per mol of the dinitrile to 1 mol per mol of dinitrile and concentrations even greater than 1 mol per mol of dinitrile, if desired. Preferably, however, from about 0.3 to about 0.7 mol of base per mol of the dinitrile is employed. Since the rate of the reaction depends on the concentration of the base one can choose any desired concentration of base which will give the desired speed of reaction. It should be noted, however, that a low yield of the monoamide could be obtained if a very strongly basic solution is used. Preferably, about a 50% solution of the base in water is employed.

The amount of 100% hydrogen peroxide which is used on a molar basis varies from, about 1.0 to about 2.5 mols per mol of the dinitrile, preferably 1.75 to 2.20 mols per mol of dinitrile. While less than 1 mol of hydrogen peroxide per mol of the dinitrile can be used, the product thus achieved would contain quantities of unreacted dinitrile, the amounts of which would depend on the degree of the deficiency in the amount of the peroxide employed. On the other hand, more than 2.5 mols of hydrogen peroxide per mol of the dinitrile can be used but increasing amounts of the peroxide would result in increasing amounts of undesired diamide in the reaction product.

The hydrogen peroxide to be used should generally be an aqueous solution containing a minimum of about 3% by weight of hydrogen peroxide. Concentrations of 50% by weight and even higher may be employed although it is preferred to use solutions containing from about 30% to about 50% by weight.

In carrying out the preparation of the azomonoamide, a solution of the diamide is prepared and the base is added, generally with rapid stirring. The hydrogen peroxide is then introduced and the reaction is allowed to continue until the evolution of oxygen ceases. Preferential conversion of only one of the cyano groups to the amide group occurs to give the monoamide in favorable proportion to the completely reacted diamide.

The resulting azomonoamide is recovered as a precipitate from the reaction mixture and has a half life in solution at 80°C. of about 10 hours.

If desired, the azomonoamide can be purified by any suitable method. Preferably, the final mixture is treated with methylene chloride to dissolve the monoamide and the dinitrile while the diamide remains undissolved. The methylene chloride is then evaporated from the mixture of the dinitrile and the azomonoamide, which mixture is then stirred into warm or hot water, preferably about 10 grams of mixture per 100 grams of water at a temperature of 60°C. is used. The dinitrile, which is insoluble in water is then filtered off and the water is cooled to 0°C. to crystallize out the monoamide.

The azomonoamide of this invention is water soluble, neutral and extremely effective as a free radical initiator. By contrast when the corresponding azodiamide compound is used, the polymerization must be carried out at higher temperatures and the diamide has been found not to possess good free radical initiating properties. In addition, the corresponding diamide decomposes on storage to yield a material which appears physically unchanged but which has a completely different set of properties from that of the original diamide.

The unique compound of this invention is an excellent initiator of the polymerization of any desired ethylenically unsaturated compounds such as the polymerizable vinyl and vinylidene compounds including, vinyl monomers, for example, butadiene, isoprene, the esters of acrylic, methacrylic and other $\alpha$-substituted acrylic acids including esters of $\alpha$-cyanoacrylic acid, acrylonitrile, methacrylonitrile and other $\alpha$-substituted acrylonitriles, vinyl esters, vinyl chloride, vinylidene chloride and any of the ethylenically unsaturated monomers listed in U.S. Pat. No. 3,225,119 issued to William P. Baker, Jr. on Dec. 21, 1965.

Since the unique initiator of this invention is water soluble, the polymerization of the ethylenically unsaturated compound may be carried out in an aqueous solution as well as in a dispersion or emulsion. In addition to water, various solvents may be employed for the polymerization such as, for example, methanol, ethanol, acetone, methylene chloride, chloroform, dioxane, tetrahydrofurane, the dimethyl ether of ethylene glycol, dimethylformamide, dimethylacetamide or any of those disclosed in British Patent No. 1,096,889.

Any suitable reaction conditions may be observed in carrying out the polymerization of the ethylenically unsaturated monomers using the unique initiator of this invention. For example, temperatures as low as 25°C. and as high as 160°C. may be employed in carrying out the polymerization, preferably 60° to about 100°C. The optimum temperature for a particular monomer will depend upon its desired reactivity. The polymerization may be carried out at atmospheric pressure, under a vacuum or at pressures above atmospheric pressure. In some instances an inert atmosphere such as nitrogen, argon and the like may be used to advantage.

The invention is further illustrated but is not intended to be limited by the following examples in which all parts and percentages are by weight unless otherwise specified.

EXAMPLE 1

Twenty-five parts of $\alpha,\alpha'$-azobisisobutyronitrile (0.152 mol) are dissolved in 225 parts of absolute methanol and 8.5 parts of a 50% solution of sodium hydroxide in water are added with stirring. To the rapidly stirred solution are added 22.5 parts of a 50% solution of hydrogen peroxide in water (0.33 mol) in about 5 minutes. Oxygen is evolved during the reaction and the temperature increases to 45°C. A clear yellow solution is obtained. The reaction is essentially complete about 5 minutes after the hydrogen peroxide addition is complete, at which point the evolution of oxygen ceases. Stirring is continued for 15 minutes longer. Liquid is removed by blowing air across the surface of the reaction mixture until no more precipitation of solid occurs. The air dried solid is extracted with methylene chloride to dissolve unreacted $\alpha,\alpha'$-azobisisobutyronitrile and the monoamide 2-[(1-cyano-1-methylethyl)azo]-2-methylpropionamide leaving $\alpha,\alpha'$-azobisisobutyramide. The methylene chloride is evaporated and the residue is treated with warm water (50°C.) to dissolve the monoamide, leaving the insoluble dinitrile behind as a precipitate. The solution is cooled to 0°C. to precipitate the monoamide. A 50% yield of monoamide is obtained, 13.7 g.

Elemental analysis of the product gave an average of carbon, hydrogen and nitrogen of 52.75, 7.80 and 30.55, respectively, against theoretical values of 52.8, 7.7 and 30.8, respectively, for the empirical formula $C_8H_{14}N_4O$. A molecular weight determination in dioxane yielded 180 against a theoretical 182. The monoamide structure was verified by nuclear magnetic resonance and infrared spectra studies. The half life of the product in water at 80°C. was determined as 11.2 hours via measurement of the decrease in UV absorption with time.

EXAMPLE 2

The preparation of Example 1 is repeated except that 25 parts of the hydrogen peroxide are employed. As a result, 16.4 g. or a 60% yield of monoamide is obtained.

The half life of the product in dimethylformamide at 80°C. was measured using ultraviolet absorption: $t_{1/2} = \ln 2/k = 11.2$ hours.

EXAMPLE 3

A mixture of 100 parts of distilled water, 1 part of ammonium lauryl sulfate and 50 parts of vinyl acetate was prepared and purged with nitrogen in a 500 ml flask containing a stirrer, a nitrogen inlet and a condenser. The flask was immersed in a steam bath. About 2.5 ml of a 1.8% aqueous solution (0.045 g.) of the product of Example 2 were added. The temperature of the reaction mixture was raised quickly to between 70° and 80°C. and stirred. After about 20 minutes the reaction mixture becomes cloudy. The reaction appears to be complete in about 1 hour but the reaction mixture is maintained at about 75°C. with stirring for a further 30 minutes. An opalescent blue emulsion is obtained which is vacuum treated to remove any trace of monomer. The emulsion is coagulated in a salt solution and the polymer is removed by filtration, washed with water and air dried. A yield of 85% of polyvinyl acetate having an inherent viscosity of 1.2 as determined in a chloroform solution (0.5%, 30°C.) is obtained.

EXAMPLE 4

The apparatus of Example 3 is flushed with nitrogen, 120 ml of water are introduced to the flask and the system is purged with nitrogen. About 0.1 part of the azoamide of Example 2 is dissolved in the water after which 2 parts of sodium lauryl sulfate and 80 parts of acrylonitrile are added. The system is again purged with nitrogen and the reaction mixture is heated to from about 65° to about 70°C. The mixture becomes milky after only a few minutes. Polymerization is allowed to proceed for 4 hours at 65° to 70°C. and a stable milky dispersion is obtained. The emulsion is coagulated in a salt solution and the polymer is removed by filtration, washed with water and air dried. A yield of 90% of polyacrylonitrile having an inherent viscosity of 8.5 as determined in dimethylformamide solution (0.5%, 30°C.) is obtained.

Although the invention has been described in considerable detail in the foregoing, it is to be understood that such detail is solely for the purposes of illustration and that variations may be by one skilled in the art without departing from the spirit and scope of the invention except as set forth in the claims.

What is claimed is:

1. A method for the emulsion polymerization of ethylenically unsaturated compounds selected from butadiene, isoprene, esters of acrylic acid and methacrylic acid, acrylonitrile, methacrylontirile, vinyl acetate, vinyl chloride, vinylidene chloride, styrene and alpha methyl styrene which comprises initiating the polymerization of the ethylenically unsaturated compound across the ethylenically unsaturated double bond in an aqueous solution with at least 0.01% by weight of

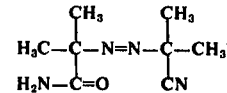

based on the weight of the ethylenically unsaturated compound.

2. The method of claim 1 wherein from about 0.01 to 2% by weight of the initiator based on the weight of the ethylenically unsaturated compound initiates the polymerization.

3. The method of claim 2 wherein 0.05 to 0.5% by weight of the initiator based on the weight of the ethylenically unsaturated compound initiates the polymerization.

4. The method of claim 1 wherein the ethylenically unsaturated compound is a polymerizable vinyl or vinylidene compound.

5. The method of claim 1 wherein the ethylenically unsaturated compound is vinyl acetate.

6. The method of claim 1 wherein the ethylenically unsaturated compound is polymerized at from 25°C. to 160°C.

7. The method of cliam 6 wherein the ethylenically unsaturated compound is polymerized at from 60°C. to 100°C.

8. The method of claim 6 wherein the ethylenically unsaturated compound is polymerized in an inert atmosphere.

* * * * *